United States Patent [19]

Matsutani et al.

[11] Patent Number: 5,069,620
[45] Date of Patent: Dec. 3, 1991

[54] DENTAL HANDPIECE

[75] Inventors: Kanji Matsutani, Tochigi; Masatoshi Fukuda, Utsunomiya, both of Japan

[73] Assignee: Matsutani Seisakusho Co., Ltd., Tochigi, Japan

[21] Appl. No.: 691,398

[22] Filed: Apr. 25, 1991

[30] Foreign Application Priority Data

May 1, 1990 [JP] Japan .................. 2-111737

[51] Int. Cl.⁵ ................................. A61C 1/12
[52] U.S. Cl. ........................................ 433/82; 433/84
[58] Field of Search .................. 433/82, 84, 85, 126, 433/127, 132

[56] References Cited

U.S. PATENT DOCUMENTS

| 3,092,908 | 6/1963 | Flatland | 433/132 |
| 3,609,058 | 9/1971 | Tarsoly | 433/132 |
| 3,762,052 | 10/1973 | Melde | 433/120 |
| 4,021,920 | 5/1977 | Kirschner et al. | 433/82 |
| 4,266,933 | 5/1981 | Warden et al. | 433/82 |
| 4,869,668 | 9/1989 | Seney | 433/85 |

FOREIGN PATENT DOCUMENTS 199550 4/1989 Japan .
1110358 4/1989 Japan .

Primary Examiner—John J. Wilson
Attorney, Agent, or Firm—Wegner, Cantor, Mueller & Player

[57] ABSTRACT

A dental handpiece includes an arm, and a hollow head formed on a distal end of the arm. The head has a nozzle projecting from an inner surface thereof. Cooling water, fed via a main coolant passageway of the arm, is injected from the nozzle. A generally cylindrical holder for supporting a dental burr is rotatably supported within the head. The cooling water injected from the nozzle passes through an auxiliary coolant passageway, formed axially through the dental burr, and is injected from a grinding portion of the dental burr. The dental handpiece also includes a pump mechanism for feeding the cooling water. Injected from the nozzle, into the auxiliary coolant passageway of the dental burr. The pump mechanism includes a screw mounted on the outer periphery of the nozzle, and a pump housing which is mounted on one end portion of the holder disposed close to the nozzle and surrounds the screw. The cooling water within the pump housing rotates in response to the rotation of the holder and the pump housing, and therefore is guided by the stationary screw to be fed into the auxiliary coolant passageway of the dental burr.

3 Claims, 3 Drawing Sheets

DENTAL HANDPIECE

BACKGROUND OF THE INVENTION

This invention relates to a dental handpiece for supporting a rotatable dental burr.

A dental handpiece comprises an elongated arm to be grasped by the dentist, and a hollow head formed at the distal end of the arm. A holder of a generally cylindrical shape is rotatably supported on the head through a pair of bearings. A shank of the dental burr is fitted in and fixed to the holder, with a grinding portion of the dental burr projected exteriorly of the head. The holder is rotated by compressed air, so that the dental burr held by the holder is rotated.

When the rotating dental burr grinds a tooth or the like, a grinding heat is produced. Therefore, it is necessary to supply cooling water (coolant) to the dental burr and the tooth so as to prevent the overheating of them. Generally, the cooling water is injected from a hole formed in that portion of the arm disposed near the head.

The following piror art disclosed dental handpieces in which cooling water is injected from a distal end portion of a dental burr so as to enhance the cooling effect.

Japanese Laid-Open (Kokai) Patent Application Nos. 99550/89 and 110358/89 (Based on these two applications and other application, U.S. Patent Application was filed Dec. 21, 1988 under Ser. No. 287,116, now U.S. Pat. No. 5,022,857) and U.S. Pat. No. 3,762,052 disclose dental burrs which have an axially-extending auxiliary coolant passageway. These prior art publications also disclose dental handpieces in which a nozzle is formed on an inner surface of a head in coaxial relation to a holder and the dental burr. An arm of the dental handpiece has a main coolant passageway extending in the longitudinal direction thereof. The proximal end of the main coolant passageway is connected to a cooling water source. The main coolant passageway extends to the head, and is connected at its distal end to the above-mentioned nozzle. The nozzle is inserted in an opening formed in one end portion of the holder disposed close to the nozzle. The cooling water of the cooling water source is injected from the nozzle via the main coolant passageway of the handpiece. The cooling water injected from the nozzle passes through the auxiliary coolant passageway of the dental burr, and is injected from the distal end of the dental burr.

The nozzle is stationary whereas the holder is rotating at high speed (for example, 300,000 r.p.m.), and therefore the outer peripheral surface of the nozzle must be kept out of contact with the inner peripheral surface of the end portion of the holder surrounding the nozzle, so that a gap is formed therebetween. Therefore, the cooling water injected from the nozzle leaks through this gap into the internal space of the head to reach one of bearings disposed close to the nozzle, thereby rusting this bearing. As a result, the rotation of the holder is affected. Also, the pressure of injection of the cooling water from the dental burr can not be kept to a sufficient level.

The above Japanese Laid-Open Patent Application No. 99550/89 discloses pump means which draws the cooling water, residing in the gap between the outer peripheral surface of the nozzle and the inner peripheral surface of the end portion of the holder surrounding the nozzle, toward the auxiliary coolant passageway of the dental burr. This pump means includes a spiral projection formed on the inner peripheral surface of the end portion of the holder. When the holder rotates, the spiral projection also rotates, and the cooling water is drawn by the rotation of the spiral projection. However, with this pump means, a suction (drawing) effect of a high level could not be obtained. The reason for this is through to be as follows. In order for the spiral projection to effect the pumping action, the spiral projection must rotate relative to the cooling water residing in the gap between the nozzle and the end portion of the holder. In other words, it is necessary that this cooling water should be stationary or be rotating at a speed lower than that of the spiral projection. Actually, however, when the holder rotates, the cooling water also rotates therewith because of the friction, and therefore the difference between the rotational speed of the cooling water and the rotational speed of the spiral projection is small, so that a high pumping action can not be obtained.

SUMMARY OF THE INVENTION

It is an object of this invention to provide a dental handpiece which can prevent or restrain cooling water from reaching a bearing, and can increase a pressure of injection of the cooling water.

According to the present invention, there is provided a dental handpiece for supporting a dental burr, the dental burr including a shank and a grinding portion extending from a distal end of the shank, the dental burr having an auxiliary coolant passageway extending along an axis of the dental burr, one end of the auxiliary coolant passageway being open to a proximal end of the shank whereas the other end thereof is open to an outer surface of the grinding portion, the dental handpiece comprising:

(a) a body including an arm, and a hollow head formed on a distal end of the arm, the head having a nozzle extending from an inner surface thereof, and the body having a main coolant passageway which extends in a longitudinal direction of the arm and is connected at its distal end to the nozzle;

(b) holder means of a generally cylindrical shape rotatably supported within the head of the body through bearing means, the shank of the dental burr being adapted to be inserted in and supported by the holder means, the holder means and the dental burr being disposed coaxially with the nozzle, and the grinding portion of the dental burr projecting exteriorly of the head; and (c) pump means for feeding cooling water, injected from the nozzle, into the auxiliary coolant passageway of the dental burr, the pump means comprising screw means mounted on an outer periphery of the nozzle, and pump housing means mounted on one end portion of the holder means disposed close to the nozzle, the pump housing means surrounding the screw means.

DESCRIPTION OF THE PREFERRED EMBODIMENTS OF THE INVENTION

The invention will now be described with reference to the drawings.

Figure 1:
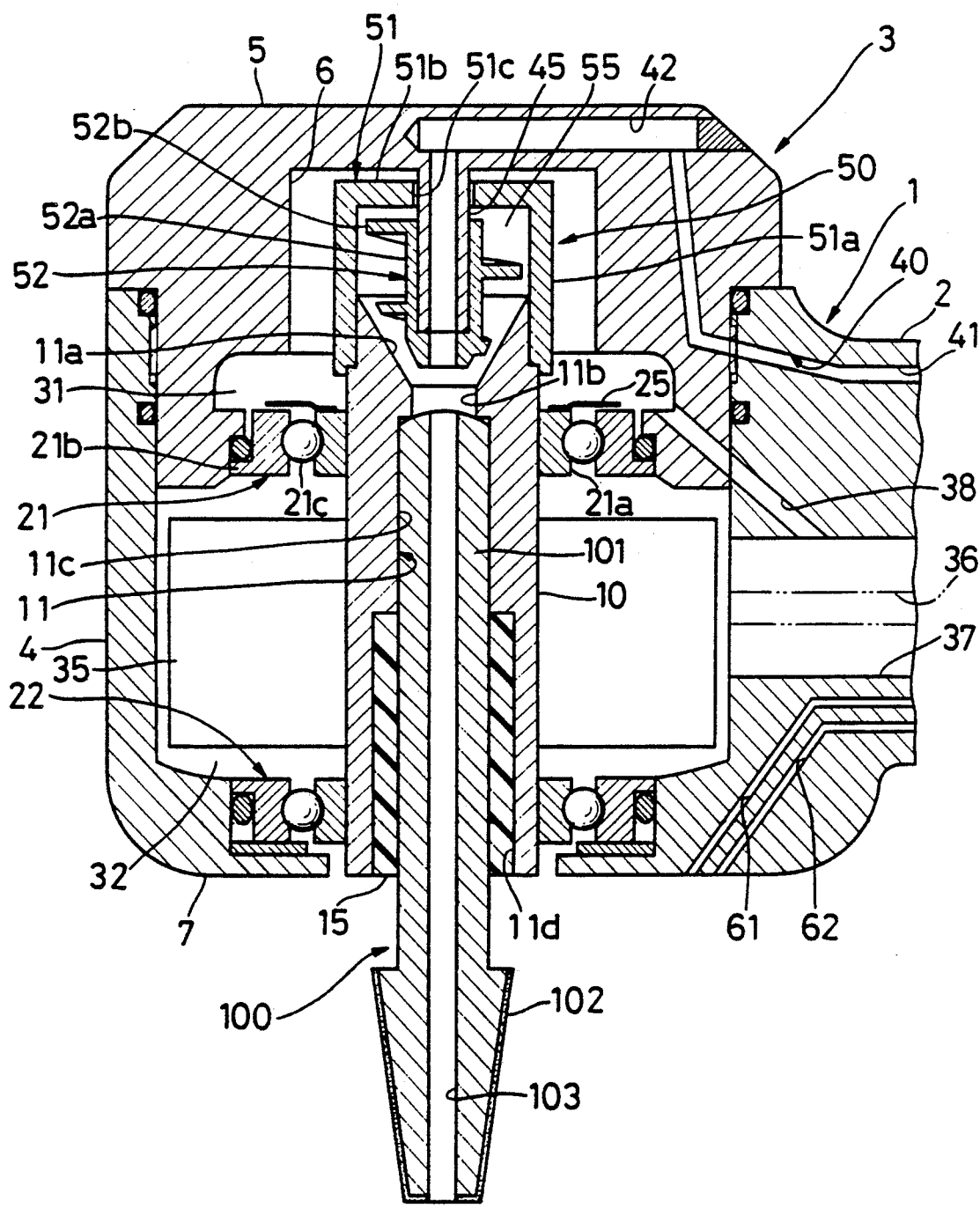
FIG. 1 is a vertical cross-sectional view of an important portion of a dental handpiece of the present invention.

As shown in FIG. 1, a dental handpiece comprises a body 1. The body 1 includes an elongated arm 2 to be grasped by the operator, and a hollow head 3 formed at the distal end of the arm 2. In FIG. 1, with respect to the arm 2, only its distal end portion is shown. The head 3 includes a cylindrical portion 4 formed integrally with the distal end of the arm 2, and a cap 5 threaded into an upper open end (FIG. 1) of the cylindrical portion 4 to close the same. A recess 6 is formed in the lower surface of the cap 5. A radially inwardly-directed flange 7 is formed on the flower end of the cylindrical portion 4.

A cylindrical holder 10 is rotatably supported on the head 3 through a pair of bearings 21 and 22. The holder 10 is disposed coaxially with the cylindrical portion 4 of the body 1. The pair of bearings 21 and 22 are spaced from each other in the axial direction of the holder 10. One bearing 21 is interposed between the inner periphery of the lower end portion of the cap 5 and the outer periphery of the holder 10. The other bearing 22 is interposed between the inner periphery of the flange 7 and the other periphery of the holder 10.

A ring-shaped seal plate 25 is mounted on the bearing 21. More specifically, the inner peripheral portion of the seal plate 25 is fixedly secured to an inner ring 21a of the bearing 21, and the outer peripheral portion of the seal plate 25 is disposed in closely spaced, opposed relation to an upper surface of an outer ring 21b of the bearing 21. The seal plate 25 covers the gap between the inner and outer rings 21a and 21b and steel balls 21c interposed between these two rings.

The internal space of the head 3 has a first chamber 31 defined by the inner surface of the recess 6 of the cap 5 and the bearing 21, and a second chamber 32 defined by the inner peripheral surface of the cylindrical portion 4 and the pair of bearings 21 and 22. In other words, the internal space of the head 3 is partitioned by the bearing 21 into the first and second chambers 31 and 32.

A plurality of blades 35 are mounted on that portion of the outer periphery of the holder 10 disposed in the second chamber 32 of the head 3. The arm 2 has an air supply passageway 36 and an exhaust passageway 37 both extending in the longitudinal direction of the arm 2. The proximal end of the air supply passageway 36 is connected to a compressed air source via a valve, mounted on the arm 2, and a tube, and the distal end of the air supply passageway 36 is connected to the second chamber 32. The proximal end of the exhaust passageway 37 is open to the exterior (i.e., the ambient atmosphere), and the distal end of the exhaust passageway 37 is connected to the second chamber 32. The compressed air is supplied via the air supply passageway 36 to the blades 35 in the second chamber 32 so as to rotate the holder 10 at high speed. As will be appreciated from this explanation, the blades 35, the air supply passageway 36 and the exhaust passageway 37 jointly constitute rotation drive means for the holder 10. The body 1 has a communication passageway 38 communicating the first chamber 31 with the exhaust passageway 37.

The holder 10 has a through hole 11 extending axially thereof. The through hole 11 has a tapered portion 11a, a smaller-diameter portion 11b, an intermediate-diameter portion 11c and a greater-diameter portion 11d which are arranged in this order from the upper end toward the lower end of the through hole 11. The tapered portion 11a is decreasing in diameter progressively downward. A cylindrical grip member 15 made of an elastic material, such as rubber, having a high coefficient of friction is fixedly fitted in the greater-diameter portion 11d. The inner diameter of the grip member 15 is slightly smaller than the inner diameter of the intermediate-diameter portion 11c.

A dental burr 100 is supported by the holder 10. The dental burr 100 has a shank 101 substantially equal in diameter to the intermediate-diameter portion 11c of the holder 10, and a grinding portion 102 having abrasive grains (made, for example, of diamond) electro-deposited on the outer surface thereof. The dental burr 100 is positioned in place by inserting the upper portion of the shank 101 into the intermediate-diameter portion 11c of the holder 10, and the dental burr 100 is caused to rotate together with the holder 10 through the friction between the lower portion of the shank 101 and the grip member 15. An auxiliary coolant passageway 103 is formed axially through the dental burr 100. One end of the auxiliary coolant passageway 103 is open to the upper end of the shank 101 to be connected to the smaller-diameter portion 11b of the through hole 11. The other end of the auxiliary coolant passageway 103 is open to the distal end face of the grinding portion 102.

A main coolant passageway 40 is formed in the body 1 of the dental handpiece. The main coolant passageway 40 has a first passageway 41 formed in the arm 2 and extending in the longitudinal direction of the arm 2, and a second passageway 42 formed in the cap 5. The proximal end of the first passageway 41 is connected to a pressurized cooling water source via a valve, mounted on the arm, and a tube. The distal end of the first passageway 41 is open to the inner peripheral surface of the cylindrical portion 4. The second passageway 42 has a portion extending in the axial direction of the cap 5, and another portion extending in the radial direction of the cap 5. One end of the second passageway 42 is open to the outer peripheral surface of the cap 5, and is connected to the distal end of the first passageway 41. The other end of the second passageway 42 is disposed at the central portion of the cap 5.

A downwardly-extending nozzler 45 is formed at the central portion of the cap 5. The nozzle 45 is disposed coaxially with the holder 10 and the dental burr 100. The upper end of the nozzle 45 is connected to the distal end of the main coolant passageway 40, that is, the other end of the second passageway 42. The lower end of the nozzler 45 is disposed in the tapered portion 11a of the through hole 11 of the holder 10.

The dental handpiece further comprises pump means 50 disposed in the first chamber 31. The pump means 50 comprises a pump housing 51 mounted on the upper end of the holder 10, and a screw 52 mounted on the nozzle 45 and received within the pump housing 51. A pump chamber 55 is formed by the inner surface of the pump housing 51 and the inner surface of the tapered portion 11a of the through hole 11 of the holder 10.

The pump housing 51 comprises a cylindrical portion 51a, and an end wall 51b formed on the upper end of the cylindrical portion 51a. The lower end of the cylindrical portion 51a is fixedly secured to the outer periphery of the upper end portion of the holder 10. A hole 51c is formed through the central portion of the end wall 51b. The nozzle 45 extends through the hole 51c of the pump housing 51 with a slight gap therebetween, and is disposed in the pump chamber 55.

Figure 2:
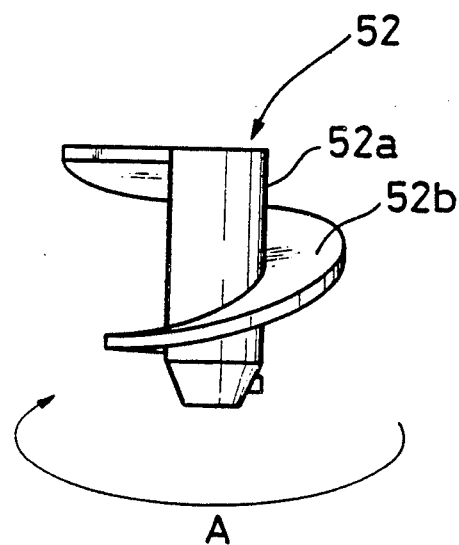
FIG. 2 is a front-elevational view of a screw used in the handpiece of FIG. 1.

As shown in FIGS. 1 and 2, the screw 52 has a cylindrical portion 52a fixedly mounted on the outer periphery of the nozzle 45, and a spiral projection 52b which is formed on and extends spirally around the outer periphery of the cylindrical portion 52a about 1.5 times. The outer diameter of the screw 52 is decreasing progressively toward its lower end. In other words, the width of the spiral projection 52b extending radially from the outer peripheral surface of the cylindrical portion 52b is decreasing progressively toward its lower end. The outer peripheral edge of the spiral projection 52b is disposed in relatively closely spaced, opposed relation to the inner surface of the cylindrical portion 51a and the inner surface of the tapered portion 11a of the through hole 11.

As is the case with the prior art, a coolant passageway 61 and a compressed air passageway 62 are formed in the body 1. These passageways 61 and 62 are used for auxiliary purposes.

When the dental handpiece of the above construction is to be used, the operator grasps the arm 2 with his hand, and the dental burr 100 in a rotating condition is brough into contact with a tooth or a crown to grind the same. The cooling water passes through the main coolant passageway 40 of the body 1, and is injected from the nozzle 45 toward the auxilary coolant passageway 103 of the dental burr 100. The thus injected cooling water passes through the auxiliary coolant passageway 103, and is injected from the opening formed in the grinding portion 102 of the dental burr 100 so as to cool the tooth and the grinding portion 102. Thus, the cooling water is supplied directly to those regions where the heat is generated by the grinding, and therefore a good cooling effect can be achieved.

Part of the cooling water injected from the nozzle 45 flows into the pump chamber 55. The cooling water in the pump chamber 55 is returned by the pumping action of the pump means 50 downward, that is, toward the auxiliary coolant passageway 103 of the dental burr 100. More specifically, when the holder 10 and the pump housing 51 rotate in a direction of arrow A (FIG. 2), the cooling water in the pump chamber 55 also rotates at high speed together with the holder 10 and the pump housing 51 in the same direction. This rotation of the cooling water is caused by the friction between the cooling water and the inner surface of the tapered portion 11a of the through hole 11 of the holder 10 and also by the friction between the cooling water and the inner surface of the cylindrical portion 51a of the pump housing 51. Since the screw 52 is stationary, the cooling water, while roatating, is guided by the screw 52 and is directed downward. Thus, a relative rotation of relatively high speed is produced between the screw 52 and the cooling water, and therefore the pumping action for the cooling water is effectively carried out. As a result, the leakage of the cooling water through the hole 51c of the pump housing 51 is either prevented to kept to a quite low level. Therefore, the rusting of the bearing 21 can be prevented.

If a small amount of cooling water leaks from the pump chamber 55 into the first chamber 31, this cooling water is dissipated by the centrifugal force produced by the rotation of the seal plate 25, thereby preventing the cooling water from intruding between the inner and outer rings 21a and 21b, and preventing the cooling water from intruding into the second chamber 32 through the gap between the inner and outer rings 21a and 21b. This cooling water is fed to the exhaust passageway 37 via the communication passageway 38, and is discharged to the exterior together with the exhaust air.

The pressure of injection of the cooling water from the distal end of the dental burr 100 can be increased by the pressure produced by the above pumping action.

Figure 3:
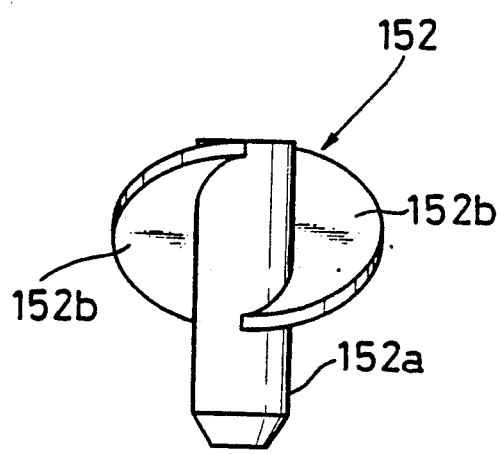
FIG. 3 is a front-elevational view of a modified screw.
Figure 4:
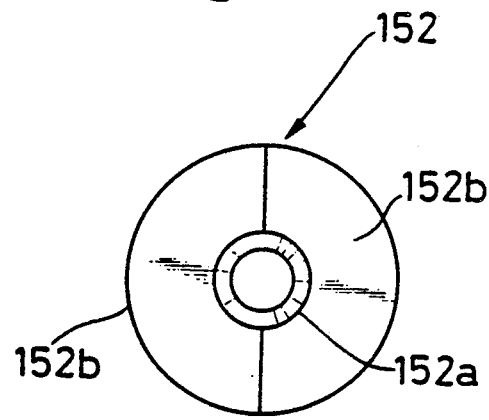
FIG. 4 is a plan view of the screw of FIG. 3.

FIGS. 3 and 4 show a modified screw 152. The screw 152 includes a cylindrical portion 152a and a pair of projections 152b. The pair of projections 152b and are spiral in the same direction, and extend respectively around halves of the outer periphery of the cylindrical portion 152a, that is, over an angle of 180° C.

Figure 5:
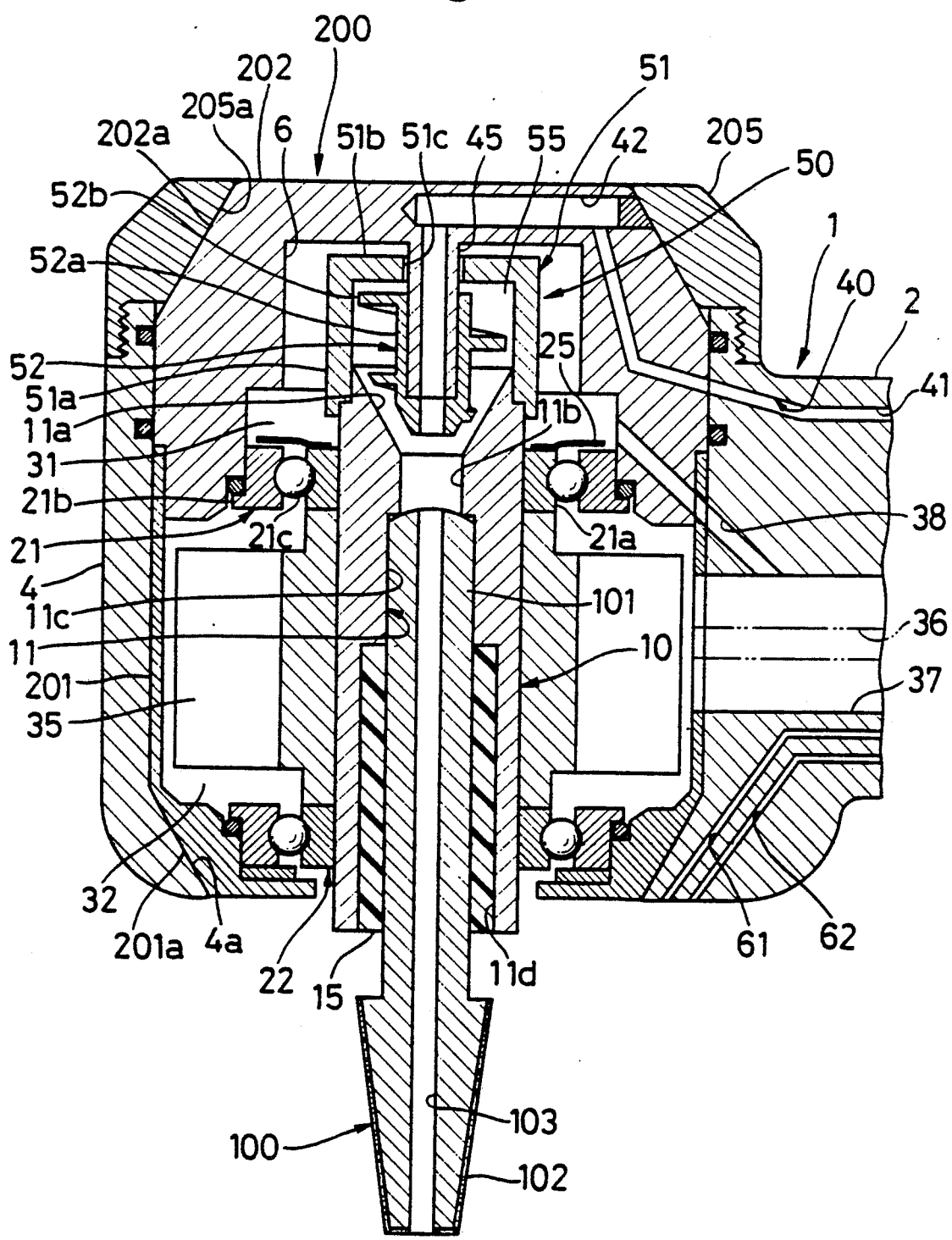
FIG. 5 is a view similar to FIG. 1, but showing a modified dental handpiece.

FIG. 5 shows a modified dental handpiece. This dental handpiece is identical in basic construction to the dental handpiece of FIG. 1, and like reference numerals denote corresponding parts, and only different portions will be described below. The dental handpiece of this embodiment includes a cartride 200. The cartride 200 comprises an inner case 201 of a generally cylindrical shape, and a cap 202 closing an open upper end of the inner case 201. A holder 10 is rotatably supported within the cartride 200 through a pair of bearings 21 and 22.

The cartridge 200 is received in a cylindrical portion 4, and is fixedly connected thereto by a fixing ring 205 threadedly engaged with the upper end portion of the cylindrical portion 4. A tapered surface 201a formed on the outer periphery of the lower end portion of the inner case 201 of the cartridge 200 is held against a tapered surface 4a formed on the inner periphery of the lower end portion of the cylindrical portion 4. A tapered surface 205a formed on the inner periphery of the fixing ring 205 is held against a tapered surface 202a formed on the outer periphery of the upper end portion of the cap 202 of the cartridge 200. The cylindrical portion 4, the cartride 200 and the fixing ring 205 jointly constitute a head of the handpiece. When the bearings 21 and 22 are exhausted, the cartride 200 is removed from the cylindrical portion 4, with the holder 10 and the bearings 21 and 22 remaining attached to the cartridge 200, and a new cartridge is attached to the cylindrical portion 4.

The present invention is not limited to the above embodiments, and various modifications can be made. For example, the holder may comprises a cylindrical member, and a collet chuck mounted in this cylinder member. The shank of the dental burr is held by this collet chuck. In this case, a push buttom for releasing the dental burr from the collet chuck is provided on the head.

What is claimed is:

1. a dental handpiece for supporting a dental burr, said dental burr including a shank and a grinding portion extending from a distal end of said shank, said dental burr having an auxiliary coolant passageway extending along an axis of said dental burr, one end of said auxiliary coolant passageway being open to a proximal end of said shank whereas the other end thereof is open to an outer surface of said grinding portion, said dental handpiece comprising:

(a) a body including an arm, and a hollow head formed on a distal end of said arm, said head having a nozzle extending from an inner surface thereof, and said body having a main coolant passageway which extends in a longitudinal direction of said arm and is connected and its distal end to said nozzle;

(b) holder means of a generally cylindrical shape rotatably supported within said head of said body through bearing means, said shank of said dental burr being adapted to be inserted in and supported by said holder means, said holder means and said dental burr being disposed coaxially with said nozzle, and said grinding portion of said dental burr projecting exteriorly of said head; and (c) pump means for feeding cooling water, injected from said nozzle, into said auxiliary coolant passageway of said dental burr, said pump means comprising screw means mounted on an outer periphery of said nozzle, and pump housing means mounted on one end portion of said holder means disposed close to said nozzle, said pump housing means surrounding said screw 2. a dental handpiece according to claim 1, in which said pump housing means comprises a cylindrical portion, and an end wall formed on one end of said cylindrical portion, the other end of said cylindrical portion being secured to said one end portion of said holder means, a hole being formed through said end wall, said nozzle extending through said hole with a gap formed therebetween, and said screw means being greater in diameter than said hole.

3. A dental handpiece according to claim 2, in which a tapered hole is formed in said one end portion of said holder means, a distal end portion of said nozzle being received in said tapered hole, and said screw means having a spiral projection decreasing progressively toward the distal end of said nozzle.

* * * * *